(12) United States Patent
Bisse

(10) Patent No.: US 10,548,312 B2
(45) Date of Patent: Feb. 4, 2020

(54) BLOOD COLLECTION DEVICE COMPRISING AN INHIBITOR OF HEXOKINASE, A GLYCOLYSIS-INHIBITING AGENT, AND AN ANTICOAGULANT OR PLASMA STABILIZER

(71) Applicant: Petra Weser-Bisse, Denzlingen (DE)

(72) Inventor: Emmanuel Bisse, Denzlingen (DE)

(73) Assignee: Petra Weser-Bisse, Denzlingen (DE)

( * ) Notice: Subject to any disclaimer, the term of this patent is extended or adjusted under 35 U.S.C. 154(b) by 78 days.

(21) Appl. No.: 15/730,588

(22) Filed: Oct. 11, 2017

(65) Prior Publication Data

US 2018/0027802 A1 Feb. 1, 2018

Related U.S. Application Data

(62) Division of application No. 14/420,528, filed as application No. PCT/EP2013/065983 on Jul. 30, 2013, now Pat. No. 9,788,538.

(30) Foreign Application Priority Data

Aug. 9, 2012 (EP) .................................... 12179907

(51) Int. Cl.

| *A01N 1/02*  | (2006.01) |
|---|---|
| *G01N 33/66* | (2006.01) |
| *G01N 33/68* | (2006.01) |
| *C12Q 1/26*  | (2006.01) |
| *C12Q 1/54*  | (2006.01) |

(52) U.S. Cl.
CPC .............. *A01N 1/0226* (2013.01); *C12Q 1/26* (2013.01); *C12Q 1/54* (2013.01); *G01N 33/66* (2013.01); *G01N 33/6815* (2013.01)

(58) Field of Classification Search
None
See application file for complete search history.

(56) References Cited

U.S. PATENT DOCUMENTS

| 4,054,488 A | 10/1977 | Marbach | |
|---|---|---|---|
| 6,913,932 B2 * | 7/2005 | Maples | A01N 1/02 252/408.1 |
| 9,788,538 B2 * | 10/2017 | Bisse | G01N 33/6815 |

OTHER PUBLICATIONS

Bishop C. Factors in the In vitro Maintenance of the Nucleotide Pattern of Whole Human Blood. Transfusion 355-359. Nov./Dec. 1961. (Year: 1961).*
PCT International Preliminary Report of Patentability including the Written Opinion of the International Searching Authority dated Feb. 19, 2015, issued on corresponding PCT International Application No. PCT/EP2013/065983.
Chan et al., "D-Mannose as a Preservative of Glucose in Blood Samples", Clinical Chemistry, vol. 38, No. 3, 1993, pp. 411-413.
Astles et al., "Stability of Plasma Lactate in Vitro in the Presence of Antiglycolytic Agents", Clinical Chemistry, vol. 40, No. 7, 1994, pp. 1327-1330.
Nauck et al., "Pre-analytical Conditions Affecting the Determination of the Plasma Homocysteine Concentration", Clinical Chemistry and Laboratory Medicine, 39(8), 2001, pp. 675-680.
Chan et al., "Effectiveness of Sodium Floride as a Preservative of Glucose in Blood", vol. 35, No. 2, 1989, pp. 315-317.
Westgard et al., "Use of the Du Pont 'Automatic Clinical Analyser' in Direct Determination of Lactic Acid in Plasma Stabilized with Sodium Fluoride", Clinical Chemistry, vol. 18, No. 11, 1972.
Bueding et al., "The Effect of Sodium Fluoride and Sodium Iodoacetate on Glycolysis in Human Blood", Journal of Biol. Chemistry, vol. 141, No. 2, 1941, pp. 1334-1338.
Le Roux et al., "A new antiglycolytic agent", Annals of Clinical Biochemistry, vol. 41, No. 1, 2004, pp. 43-46, Abstract.
Gambino et al., "Acidification of Blood is Superior to Sodium Fluoride alone as an inhibitor of Glycolysis", Clinical Chemistry, vol. 55, No. 5, 2009, pp. 1019-1021.
P. McLean, "Carbohydrate Metabolism of Mammary Tissue—I. Pathways of Glucose Catabolism in the Mammary Gland", Biochimica et Biophysica Acta, vol. 30, No. 2, 1958, pp. 303-315.
Bishop, C., "Factors in the In Vitro Maintenance of the Nucleotide Pattern of Whole Human Blood", Transfusion, 1 (Nov.-Dec.), 1961, pp. 355-359.
Walaas & Walaas, "The Activation of Muscle Hexokinase by Divalent Metal Ions", ACTA Chemica Scandinavica, vol. 16, No. 7, 1962, pp. 1682-1694.
Long, C., "Studies Involving Enzymic Phosphorylation—1. The Hexokinase Activity of Rat Tissues", Biochemistry J., vol. 50, 1952, pp. 407-415.
Horton et al., "Enzymic and Cerebral Metabolic Effects of 2-Deoxy-D-Glucose", Journal of Neurochemistry, vol. 21, 1973, pp. 507-520.
International Search Report issued in PCT/EP2013/065983, dated Mar. 12, 2013.

* cited by examiner

*Primary Examiner* — Ralph J Gitomer
(74) *Attorney, Agent, or Firm* — Locke Lord LLP; Scott D. Wofsy; Nicholas J. DiCeglie, Jr.

(57) ABSTRACT

The present invention relates to a composition for the stabilization of glucose, lactate and homocysteine in blood after collection, to a use of the provided compositions and a method for the stabilization of glucose, lactate and homocysteine in blood after collection, as well as optionally the in vitro determination of glucose, lactate and homocysteine in blood, and a blood collection device provided for said use and method.

10 Claims, 3 Drawing Sheets

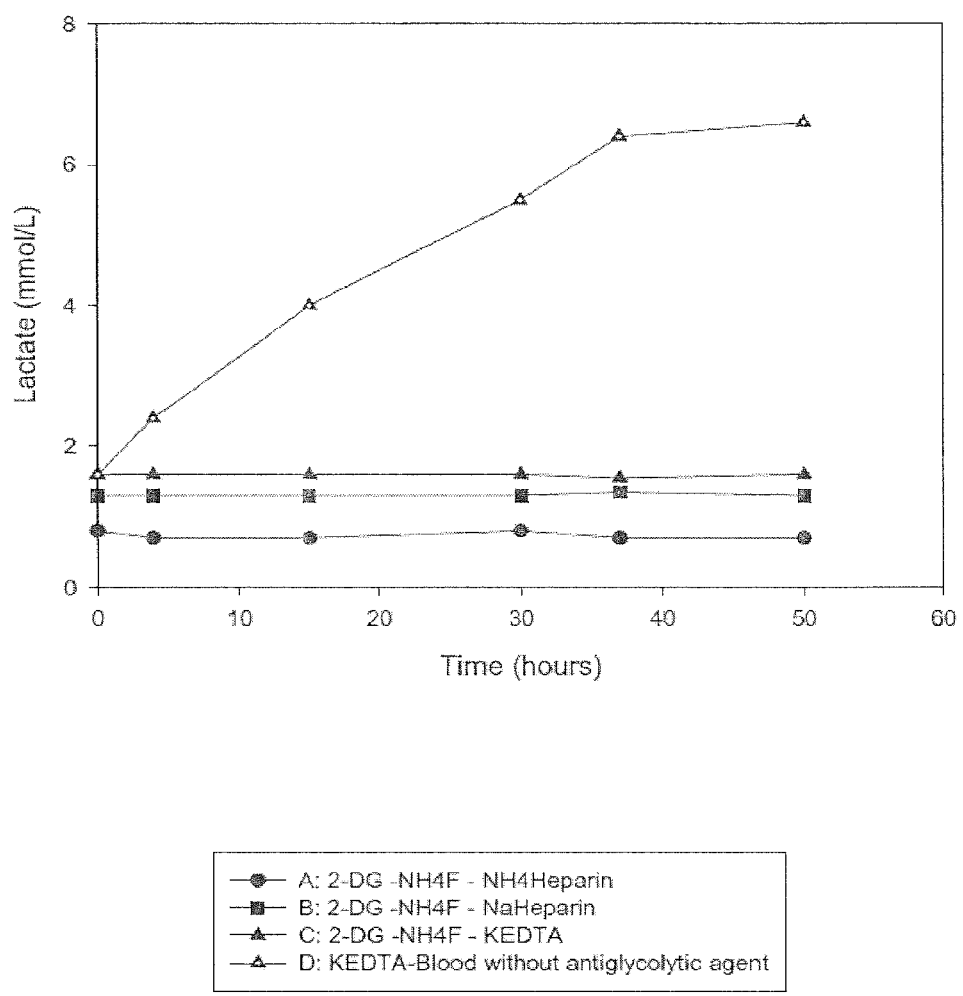

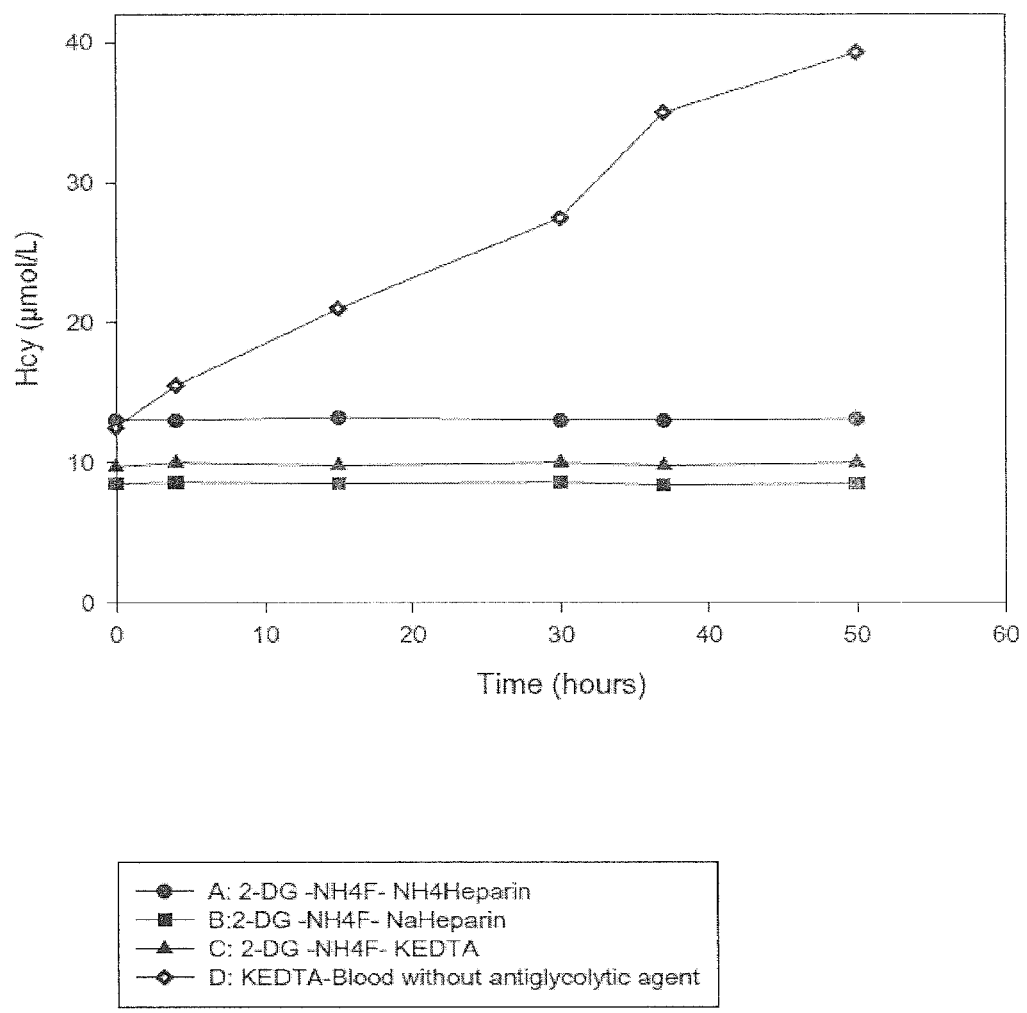

BLOOD COLLECTION DEVICE COMPRISING AN INHIBITOR OF HEXOKINASE, A GLYCOLYSIS-INHIBITING AGENT, AND AN ANTICOAGULANT OR PLASMA STABILIZER

This Application is a Division of U.S. patent application Ser. No. 14/420,528, filed on Feb. 9, 2015, which application is the national phase under 35 U.S.C. § 371 of PCT International Application No. PCT/EP2013/065983, which has an International filing date of Jul. 30, 2013, which claims priority to European Patent Application No. 12179907.6, filed Aug. 9, 2012. The entire contents of these applications are incorporated herein by reference in their entirety.

FIELD OF THE INVENTION

The present invention relates to the ex vivo stabilization and storage of blood. In particular, the present invention relates to a composition for the stabilization of glucose, lactate and homocysteine in blood after collection, to a use of the provided compositions and a method for the stabilization of glucose, lactate and homocysteine in blood after collection, as well as optionally the in vitro determination of glucose, lactate and homocysteine in blood, and a blood collection device provided for said use and method.

BACKGROUND OF THE INVENTION

Blood sampling and testing are routinely carried out for various diagnostic purposes. Detection and quantification of glucose in blood is for example used in the diagnosis and management of disorders of carbohydrate metabolism such as diabetes mellitus. Determination of lactate in blood may for example be used to test acid-base homeostasis and to screen for lactic acidosis, hypoxia or sepsis, and to evaluate adaptation to exercise. An increased level of plasma total homocysteine (tHcy) is for example a risk factor for cardiovascular disease and a sensitive marker for vitamin B deficiencies. In order to be useful diagnostic indicators and predictors, the levels of such blood components should be determined accurately and precisely.

Since metabolism in blood cells (erythrocytes, leukocytes and platelets) is ongoing ex vivo, i.e. after blood collection, levels of blood glucose, lactate and homocysteine can change significantly during the time elapsed between withdrawal and analysis, potentially leading to erroneous results, especially when the time elapsed is variable and uncontrolled and when storage conditions such as temperature vary. Due to continued glycolysis in blood cells, mainly in the erythrocytes, the concentration of blood glucose decreases after collection. Chan et al. in Clinical Chemistry, 38, 1992, pp. 411-413 reported that the plasma glucose concentration in heparinized blood samples at room temperature decreases at a rate of approximately 0.3 mmol/L per hour during the first 12 hours after blood collection. The decrease in blood glucose is accompanied by an increase in lactate concentration. Astles et al. in Clinical Chemistry, 40, 1994, pp. 1327-1330 indicated the increase in lactate to be 0.7 mmol/L per hour, which is large in view of the cited reference interval of 0.5-2.2 mmol/L for lactate. Because of ongoing homocysteine metabolism, wherein homocysteine is formed from methionine via adenosylmethionine-dependent methyl transfer reactions, and ongoing release of homocysteine from erythrocytes, tHcy increases after blood collection. Nauck et al. in Clinical Chemistry and Laboratory Medicine, 39, 2001, pp. 675-680 reported that at room temperature the concentration of tHcy increases by approximately 1-2 µmol/L per hour during the first hours, which corresponds to an approximately 10% increase of tHcy per hour. This means typically after blood collection glucose is continuously consumed by the blood cells and lactate and homocysteine are released from the blood cells.

The changes in glucose, lactate and homocysteine levels in blood after collection are time- and temperature-dependent. Plasma concentration changes of these substances can be prevented by the immediate centrifugation and removal of the blood cells. This requires the addition of anticoagulant, such as EDTA salt, citrate salt, oxalate salt and heparin salt, to the whole blood. Moreover, a centrifuge and the capacity for immediate processing need to be available at or close to the site of blood collection which can be problematic and impractical. Blood samples can be cooled on ice until centrifugation to reduce changes in glucose, lactate and homocysteine levels. However, chilling on ice may not be sufficient and may be impossible or impractical, for example when there is a substantial delay between the collection and the processing and analysis, or when many samples have to be collected and transported. For blood serum, changes in glucose, lactate and homocysteine levels can occur because serum is prepared from a blood sample left at room temperature for a time sufficient to allow coagulation (c. 20-60 min), and centrifugation and separation of the blood cells is possible only thereafter. Preanalytical sample processing can interfere in the subsequent testing for glucose, lactate and homocysteine or co-analytes. For example, disturbance of cellular integrity such as hemolysis may be problematic. Furthermore, time-consuming or error-prone processing steps, for example deproteination using trichloroacetic acid, may not be suitable in routine clinical processing.

When a blood sample cannot be separated or cooled immediately after collection, in addition to an anticoagulant an antiglycolytic agent such as iodoacetate, mannose or fluoride as stabilizer can be added. However, mannose can interfere with enzymatic analysis methods using glucose oxidase or hexokinase. Fluoride stabilizes glucose primarily by inhibiting enolase in the glycolytic pathway. Chan et al. in Clinical Chemistry, 35, 1989, pp. 315-317 showed that fluoride does not prevent loss of plasma glucose completely and that at room temperature the concentration of glucose in blood containing fluoride decreases significantly for the first four hours after collection. Westgard et al. in Clinical Chemistry, 18, 1972, pp. 1334-1338 described that whole blood stabilized with sodium fluoride and separated within 15 min provides an acceptable sample for lactate determination. However, for the case without separation Astles et al. reported that for blood samples with sodium fluoride and potassium oxalate at room temperature lactate increased by 0.2 mmol/L after 1 hour post-collection. Fluoride, adenosine analogues such as 3-deazaadenosine or citrate are used to stabilize tHcy after blood collection, but the use of stabilizers usually leads to deviations at baseline and the problem with stabilization of tHcy is only partly solved. Some typically used stabilizers of tHcy can affect analytical techniques such as fluorescence polarization immunoassay, chemiluminescence immunoassay and enzyme linked immunoassay (see e.g. Nauck et al.).

The use of two agents for the inhibition of glycolysis in blood samples has been considered. Chan et al. (1992) reported the use of sodium fluoride and mannose, but stabilization of the blood glucose concentration was incomplete. Moreover, mannose can interfere with enzymatic analysis methods using glucose oxidase or hexokinase. Bueding and Goldfarb in Journal of Biological Chemistry, 141, 1941, pp. 539-544 demonstrated the use of sodium iodoacetate and sodium fluoride to preserve glucose and lactate. The use of glyceraldehyde and sodium fluoride for the preservation of plasma glucose concentrations was reported by le Roux et al. in Annals of Clinical Biochemistry, 41, 2004, pp. 43-46. Glucose stabilization using sodium fluoride and acidification with citric acid was described by Gambino et al. in Clinical Chemistry, 55, 2009, pp. 1019-1021. However, while these studies aimed at stabilizing glucose and/or lactate, in vitro stabilization of glucose, lactate and homocysteine in blood has not been addressed.

There is a need in the art to make more robust and to simplify preanalytics for the accurate testing of blood glucose, lactate and homocysteine while avoiding cumbersome, complicated, error-prone, costly, impractical or time-critical near-collection processing such as immediate centrifugation or icing of blood samples and providing benefits in terms of improved handling, storage and transport of said samples as well as sample throughput. In particular, the object of the present invention is to effect sufficient and predictable inhibition of glycolysis and to efficiently stabilize blood glucose, lactate and homocysteine in blood after collection at room temperature enabling prolonged storage of blood and allowing blood glucose, lactate and homocysteine and other substances to be determined accurately and reliably using a single sample.

SUMMARY OF THE INVENTION

The object is solved by the in vitro methods according to claims 1 and 12, the uses according to claims 13 and 20, the blood collection device according to claim 16, the kit according to claim 17 and the composition according to claim 18, while preferred embodiments are provided in the dependent claims and are further described below.

The present invention in particular provides the following items including main aspects and preferred embodiments, which respectively alone and in combination particularly contribute to solving the above object and eventually provide additional advantages:

(1) A method for the treatment of a blood sample in vitro, wherein blood is mixed in vitro with a composition comprising
  i) at least one inhibitor of hexokinase;
  ii) at least one glycolysis-inhibiting agent having activity for another enzyme involved in glucose catabolism; and
  optionally iii) an anticoagulant and/or a plasma stabilizer, and
  wherein said blood sample is preserved for further analysis.

(2) The method according to item (1), wherein one and/or more of glucose, lactate and homocysteine in the blood sample is (are) stabilized, preferably glucose is stabilized.

(3) The method according to item (1) or (2), wherein the composition further comprises iv) ammonium salt $NR_4X$, wherein each R independently is hydrogen, linear $C_1$-$C_6$ alkyl, branched $C_3$-$C_6$ alkyl, unsubstituted phenyl or substituted phenyl, and X is halide, hydroxide, $C_1$-$C_4$ alkoxide and acetate, and wherein preferably each R independently is hydrogen, methyl or ethyl, and X is fluoride or chloride, and wherein more preferably $NR_4X$ is tetramethylammonium fluoride, tetramethylammonium chloride, tetraethylammonium chloride or $NH_4Cl$.

(4) The method according to item (3), wherein the concentration of the ammonium salt $NR_4X$ is 0.01 to 100 µmol/mL blood, preferably is 0.1 to 10 µmol/mL blood, and more preferably is 0.5 to 1 µmol/mL blood.

(5) The method according to any one of the preceding items, wherein the at least one inhibitor of hexokinase i) is selected from the group consisting of 2-deoxy-D-glucose, 2-fluoro-2-deoxy-D-glucose, 2-amino-2-deoxy-D-glucose and 3-bromopyruvic acid or salt thereof.

(6) The method according to any one of the preceding items, wherein the at least one glycolysis-inhibiting agent ii) has antiglycolytic activity for any one of the enzymes in the glycolytic pathway downstream of hexokinase.

(7) The method according to any one of the preceding items, wherein the at least one glycolysis-inhibiting agent ii) is selected from the group consisting of fluoride salt, iodoacetic acid or salt thereof, oxamic acid or salt thereof and dichloroacetic acid or salt therof.

(8) The method according to any one of the preceding items, wherein the anticoagulant iii) is selected from the group consisting of EDTA salt, citrate salt, oxalate salt and heparin salt.

(9) The method according to any one of items (5), (7) or (8), wherein salt as set forth in any one of items (5), (7) or (8) is salt of $NR_4^+$, wherein each R independently is hydrogen, linear $C_1$-$C_6$ alkyl, branched $C_3$-$C_6$ alkyl, unsubstituted phenyl or substituted phenyl, and wherein preferably each R independently is hydrogen, methyl or ethyl, and wherein more preferably $NR_4^+$ is tetramethylammonium ion, tetraethylammonium ion or $NH_4^+$, and wherein most preferably $NR_4^+$ is $NH_4^+$.

(10) The method according to any one of the preceding items, wherein the mass concentration of the at least one inhibitor of hexokinase i) is at least 0.01 mg/mL blood and wherein the mass concentration of the at least one glycolysis-inhibiting agent ii) is at least 0.01 mg/mL blood.

(11) The method according to any one of the preceding items, wherein the mass concentration of the at least one inhibitor of hexokinase i) is at least 0.01 mg/mL blood, more preferably is at least 0.02 mg/mL blood, even more preferably is in a range from 0.02 to 25 mg/mL blood and most preferably is in a range from 0.02 to 4 mg/mL blood, wherein the mass concentration of the at least one glycolysis-inhibiting agent ii) is at least 0.01 mg/mL blood, more preferably is at least 0.02 mg/mL blood, even more preferably is in a range from 0.02 to 25 mg/mL blood and most preferably is in a range from 0.02 to 4 mg/mL blood,
wherein optionally the mass concentration of the optional anticoagulant iii) is at least 0.01 mg/mL blood, more preferably is at least 0.1 mg/mL blood, even more preferably is in a range from 0.1 to 25 mg/mL blood and most preferably is in a range from 1 to 2.5 mg/mL blood with or 12 to 30 IU/mL blood,
and wherein preferably the ratio of the mass concentrations of the at least one inhibitor of hexokinase i) and the at least one glycolysis-inhibiting agent ii) is in a range from 100:1 to 1:100, more preferably is in a range from 50:1 to 1:50, even more preferably is in a range from 25:1 to 1:25 and most preferably is in a range from 10:1 to 1:10.

(12) The method according to any one of the preceding items, wherein the composition is in solid form, lyophilized form or in solution, and wherein in a case of a solution water or dilute acidic aqueous solution is preferred.

(13) The method according to any one of the preceding items, wherein the composition is substantially free of agents for the lysis of blood cells.
(14) The method according to any one of the preceding items, further containing a buffer and/or an additive commonly used for preserving blood, preferably in a content of up to 50% by weight.
(15) A method for the inhibition of glycolysis and optionally coagulation in a blood sample in vitro, wherein blood is mixed after its withdrawal with the composition as set forth in any one of items (1) to (14).
(16) An in vitro diagnostic method, wherein the amount(s) of blood component(s) is (are) determined in a stabilized blood sample mixed with the composition as set forth in any one of items (1) to (14).
(17) The method according to item (15) or (16), wherein one and/or more of glucose, lactate and homocysteine are stabilized.
(18) The method according to any one of items (15) to (17), wherein one and/or more of glucose, lactate and homocysteine are stabilized at room temperature for up to 50 hours after blood collection.
(19) The method according to any one of items (15) to (18), wherein glucose, lactate and homocysteine are stabilized simultaneously.
(20) The method according to any one of the preceding items, wherein the amount of one and/or more of glucose, lactate and homocysteine in blood and/or other blood component(s) are determined by comprising the following steps:
  (a) providing a blood collection device comprising, placed in the device, the composition as set forth in any one of items (1) to (14);
  (b) placing blood in the blood collection device;
  (c) mixing the composition as set forth in any one of items (1) to (14) with blood in the blood collection device;
  optionally (d) storing the blood in the blood collection device for a predetermined period of time during which glucose, lactate and homocysteine levels are substantially constant; and
  (e) determining the amount of one and/or more of glucose, lactate and homocysteine and/or other blood component(s) in the blood sample.
(21) The method according to item (20), wherein, instead of steps (a) and (b), a step is carried out which comprises placing blood in a blood collection device and subsequently placing a composition of the present invention in the blood collection device.
(22) The method according to item (20) or (21), wherein the mass concentration of the at least one inhibitor of hexokinase i) is at least 0.01 mg/mL blood, more preferably is at least 0.02 mg/mL blood, even more preferably is in a range from 0.02 to 25 mg/mL blood and most preferably is in a range from 0.02 to 4 mg/mL blood,
  wherein the mass concentration of the at least one glycolysis-inhibiting agent ii) is at least 0.01 mg/mL blood, more preferably is at least 0.02 mg/mL blood, even more preferably is in a range from 0.02 to 25 mg/mL blood and most preferably is in a range from 0.02 to 4 mg/mL blood,
  wherein optionally the mass concentration of the optional anticoagulant iii) is at least 0.01 mg/mL blood, more preferably is at least 0.1 mg/mL blood, even more preferably is in a range from 0.1 to 25 mg/mL blood and most preferably is in a range from 1 to 2.5 mg/mL blood or 12 to 30 IU/mL blood,
  and wherein preferably the ratio of the mass concentrations of the at least one inhibitor of hexokinase i) and the at least one glycolysis-inhibiting agent ii) is in a range from 100:1 to 1:100, more preferably is in a range from 50:1 to 1:50, even more preferably is in a range from 25:1 to 1:25 and most preferably is in a range from 10:1 to 1:10.
(23) The method according to any one of items (20) to (22), wherein step (d) is carried out at room temperature for up to 50 hours.
(24) The method according to any one of items (20) to (23), wherein the blood in step (b) is whole blood.
(25) The method according to any one of items (20) to (24), wherein glucose, lactate and homocysteine in step (e) are plasma glucose, plasma lactate and plasma homocysteine respectively.
(26) The method according to any one of items (20) to (25), wherein in step (e) the determination of the amount(s) of the respective blood component(s) is carried out using conventional physical, chemical, enzymatic and/or immunological methods, including combinations thereof.
(27) The method according to any one of the preceding items, wherein lysis of blood cells is substantially inhibited, and preferably lysis of blood cells is inhibited.
(28) A use of the composition as set forth in any one of items (1) to (14) for the inhibition of glycolysis and optionally coagulation in a blood sample in vitro.
(29) The use according to item (28), wherein any one of glucose, lactate and homocysteine is stabilized in blood.
(30) The use according to item (28), wherein any combination of glucose, lactate and homocysteine is stabilized.
(31) The use according to item (28), wherein glucose, lactate and homocysteine are stabilized simultaneously.
(32) The use according to any one of item (28) to (31), wherein glucose, lactate and/or homocysteine are stabilized at room temperature for up to 50 hours after blood collection.
(33) The use according to any one of item (28) to (32), wherein, concurrently with or subsequently to the use of a composition as set forth in any one of items (1) to (14), (a) test(s) is (are) carried out for the determination of one and/or more of glucose, lactate and homocysteine and optionally a further blood component.
(34) A blood collection device comprising the composition as set forth in any one of items (1) to (14).
(35) The blood collection device according to item (34), comprising a device which is capable of being connected with a conventional blood withdrawal device.
(36) A use of the blood collection device according to item (34) or (35) for stabilization and/or storage of a blood sample in vitro.
(37) The use according to item (36), wherein the blood sample is stabilized and/or stored at room temperature for up to 50 hours after blood collection.
(38) The use according to item (36) or (37), wherein, concurrently with or subsequently to the use of a composition as set forth in any one of items (1) to (14), (a) test(s) is (are) carried out for the determination of one and/or more of glucose, lactate and homocysteine and optionally a further blood component.
(39) A kit comprising:
  the blood collection device according to item (34) or (35), and
  test substances for the determination of at least one of, optionally all simultaneously, glucose, lactate and homocysteine and optionally a further blood component in collected blood.

(40) A composition as set forth in any one of items (1) to (14) for the stabilization of one and/or more of glucose, lactate and homocysteine in blood.
(41) The composition according to item (40), wherein the at least one glycolysis-inhibiting agent ii) is $NH_4F$.
(42) A use of at least one glycolysis-inhibiting agent for the stabilization and ex vivo determination of homocysteine in blood after withdrawal.
(43) The use according to item (42), wherein the at least one glycolysis-inhibiting agent has activity for an enzyme involved in glucose catabolism.
(44) The use according to item (42), wherein the at least one glycolysis-inhibiting agent has antiglycolytic activity for any one of the enzymes in the glycolytic pathway.
(45) The use according to item (44), wherein the at least one glycolysis-inhibiting agent is at least one inhibitor of hexokinase.

DETAILED DESCRIPTION OF THE INVENTION

In the following, the present invention is described in more detail while referring to preferred embodiments and examples, which are presented however for illustrative purposes and shall not be construed to limit the invention in any way.

A first aspect of the present invention is a method for the treatment of a blood sample in vitro, wherein blood is mixed in vitro with a composition comprising at least one inhibitor of hexokinase, at least one glycolysis-inhibiting agent having activity for another enzyme involved in glucose catabolism and optionally an anticoagulant and/or a plasma stabilizer, and wherein said blood sample is efficiently preserved for further analysis.

According to the invention, glycolysis and optionally coagulation are efficiently inhibited in a blood sample in vitro when blood is mixed after its withdrawal with the composition according to the present invention. In particular, one and/or more of glucose, lactate and homocysteine in the blood sample are thus stabilized.

The composition according to the invention is provided for the stabilization of one and/or more of, preferably all of, glucose, lactate and homocysteine in blood, wherein the composition comprises at least one inhibitor of hexokinase, at least one glycolysis-inhibiting agent having activity for another enzyme involved in glucose catabolism and optionally an anticoagulant and/or a plasma stabilizer. Stabilization in blood in vitro can thus be achieved.

Hexokinase catalyzes the first step in glycolysis, i.e. the metabolic pathway that converts glucose to pyruvate, said first step being the phosphorylation of glucose. Glucose and glucose 6-phosphate can be catabolized, i.e. broken down to provide energy but also to serve as a source of carbon, and they are also involved in several metabolic pathways other than glycolysis. Surprisingly, it was found in the present invention that a composition comprising a combination of at least one inhibitor of hexokinase and at least one agent having activity for another enzyme involved in glucose catabolism with an inhibitory effect on glycolysis stabilizes one and/or more of glucose, lactate and homocysteine in blood after collection particularly efficiently, fast and continuously.

This is unexpected considering in particular that substances known and used in the art such as fluoride, iodoacetate or mannose have been demonstrated to be insufficient by resulting in a decrease in blood glucose concentration with time. Even compositions with two agents for the inhibition of glycolysis known in the art, while potentially having improved antiglycolytic action compared to cases where only one antiglycolytic agent is used, may on the one hand still not be efficient in the early time intervals after blood collection (iodoacetate and fluoride) or on the other hand be unspecific and thus not well controlled or predictable in their inhibition (glyceraldehyde and fluoride; fluoride and acidification). Furthermore, prior to the particular combination of the present invention an efficient stabilization has been not only affected by insufficient inhibition of glycolysis, but factors such as loss of cellular integrity, change in osmolarity and ion leakage as well as interference in subsequent analyte testing also need to be taken into account. For example, excessive acidification and use of glyceraldehyde can interfere in the determination of lactate.

According to a particularly advantageous embodiment blood is mixed in vitro with a composition that comprises not only the at least one inhibitor of hexokinase, the at least one glycolysis-inhibiting agent having activity for another enzyme involved in glucose catabolism and optionally the anticoagulant and/or the plasma stabilizer, but furthermore an ammonium salt $NR_4X$, wherein each R independently is hydrogen, linear $C_1$-$C_6$ alkyl, branched $C_3$-$C_6$ alkyl, unsubstituted phenyl or substituted phenyl, and X is halide, hydroxide, $C_1$-$C_4$ alkoxide and acetate. Preferably each R independently is hydrogen, methyl or ethyl, and X is fluoride or chloride. More preferably $NR_4X$ is tetramethylammonium fluoride, tetramethylammonium chloride, tetraethylammonium chloride or $NH_4Cl$. The concentration of the ammonium salt $NR_4X$ is not particularly limited. In particular, the upper limit is not especially limited. A lower preferred limit is 0.01 µmol/mL blood. In a preferred embodiment the concentration of the ammonium salt $NR_4X$ is 0.01 to 100 µmol/mL blood, more preferably is 0.1 to 10 µmol/mL blood, and even more preferably is 0.5 to 1 µmol/mL blood.

According to the present invention, preferably lysis of blood cells is substantially avoided, and more preferably lysis of blood cells is avoided. Preferably, lysis of blood cells is substantially inhibited, and more preferably lysis of blood cells is inhibited. The composition of the invention therefore is preferably substantially free of agents for the lysis of blood cells, and more preferably is free of agents for the lysis of blood cells.

Surprisingly, it was found that when the ammonium salt iv) of the invention is additionally comprised in the composition hemolysis can be efficiently and effectively inhibited (see also Examples 10-13 and Table 10). This advantageous effect is especially relevant in cases where occurrence of hemolysis must be significantly reduced or even safely and surely avoided, or where presence of agents which may affect cellular stability cannot be entirely ruled out or avoided. Hemolysis can significantly further destabilize the sample and prevent prolonged storage. Furthermore, hemolysis can be detrimental to blood testing and diagnostics because, for example, mixing of plasma components with cellular components from the lysed cells can lead to spurious results for both plasma and cell analyses or even prevent such analyses altogether. Therefore, inhibiting hemolysis is advantageous for the reliable determination of blood components.

Therefore, the provision of the ammonium salt iv) as a further additive provides significant further benefits. In particular, one and/or more of glucose, lactate and homocysteine, preferably all, in the blood sample is (are) stabilized, while furthermore the inhibition of hemolysis can be significantly enhanced. This further improved stabilization and preservation of a blood sample can provide longer storage and a more reliable determination of blood components and thus improved diagnostics.

In an embodiment the at least one inhibitor of hexokinase is selected from the group consisting of 2-deoxy-D-glucose, 2-fluoro-2-deoxy-D-glucose, 2-amino-2-deoxy-D-glucose and 3-bromopyruvic acid or salt thereof. 2-deoxy-D-glucose, 2-fluoro-2-deoxy-D-glucose and 2-amino-2-deoxy-D-glucose are glucose analogues and hexokinase inhibitors that can be phosphorylated but not metabolized. 3-bromopyruvic acid is a strong alkylating agent which inhibits hexokinase.

In one embodiment the at least one glycolysis-inhibiting agent has antiglycolytic activity for any one of the enzymes in the glycolytic pathway downstream of hexokinase, comprising phosphoglucose isomerase, phosphofructokinase, aldolase, triose phosphate isomerase, glyceraldehyde 3-phosphate dehydrogenase, phosphoglycerate kinase, phosphoglycerate mutase, enolase and pyruvate kinase. In another, optionally combined embodiment the at least one glycolysis-inhibiting agent is selected from the group consisting of fluoride salt, iodoacetic acid or salt therof, oxamic acid or salt thereof and dichloroacetic acid or salt therof. Fluoride has an inhibitory effect on enolase, iodoacetate inhibits glyceraldehyde 3-phosphate dehydrogenase, while oxamate inhibits lactate dehydrogenase which catalyzes the conversion of pyruvate to lactate. Dichloroacetate stimulates the activity of pyruvate dehydrogenase by inhibiting pyruvate dehydrogenase kinase thus decreasing lactate formation.

The inhibitor of hexokinase preferably is a reversible or irreversible inhibitor of hexokinase, wherein hexokinase comprises the isoforms or isozymes of said enzyme, including glucokinase. In the case of reversible inhibition, inhibition may be competitive, uncompetitive, mixed and non-competitive.

Preferably, inhibitor of hexokinase is specific, i.e. inhibition is different from irreversible enzyme inactivation by non-specific effect(s) such as generally destroying protein structure or denaturation, for example caused by changes of pH or temperature. The inhibitory effect of an inhibitor of hexokinase can be tested by providing said inhibitor, a hexose, preferably glucose, as a substrate, ATP and hexokinase in vitro, preferably in physiological or near-physiological conditions, and measuring the time-dependent concentration of the hexose and phosphorylated hexose, wherein an inhibitory effect is present when the hexose concentration decreases with time more slowly or not at all and/or the concentration of phosphorylated hexose increases with time more slowly or not at all compared to a system lacking the inhibitor.

The glycolysis-inhibiting agent having activity for another enzyme involved in glucose catabolism preferably is a specific enzyme inhibitor and/or enzyme activator for any one of the enzymes involved in glucose catabolism, wherein said agent inhibits glycolysis. In the case of an enzyme inhibitor, inhibition can be irreversible or reversible, wherein reversible inhibition may be competitive, uncompetitive, mixed and non-competitive. Preferably, the enzyme inhibitor is specific, i.e. inhibition is different from irreversible enzyme inactivation by non-specific effect(s) such as generally destroying protein structure or denaturation, for example caused by changes of pH or temperature. In the case of an enzyme activator, said activator preferably is an agent that interacts specifically with an enzyme and increases the activity of the latter, for example through an allosteric effect. The inhibitory effect of the glycolysis-inhibiting agent on glycolysis can be tested by monitoring over time glucose and/or pyruvate or respectively lactate concentrations.

The optional anticoagulant is preferably present and is typically further to/other than the at least one inhibitor of hexokinase and the at least one glycolysis-inhibiting agent, more preferably is selected from the group consisting of EDTA salt, citrate salt, oxalate salt and heparin salt. In one embodiment, lithium heparinate or ammonium heparinate and EDTA salt are more preferred, and in particular lithium heparinate or ammonium heparinate is most preferred, because it is amenable to the determination of a multitude of co-analytes, while for example EDTA salt may limit the number of determinable analytes. Unexpectedly, it was found in the present invention that when the composition of the invention comprises heparinate, then glucose, lactate and homocysteine are stabilized particularly fast, efficiently and continuously.

In the case that one and/or more of the at least one inhibitor of hexokinase, the at least one glycolysis-inhibiting agent having activity for another enzyme involved in glucose catabolism and optionally the anticoagulant and/or the plasma stabilizer is (are) provided as salt, in particular salts as set forth in items (5), (7) and (8), hemolysis can unexpectedly and advantageously be significantly inhibited by providing at least one salt of said agents as an ammonium salt (see also Examples 8 and 9, and Table 10). Ammonium salt denotes a salt of $NR_4^+$, wherein each R independently is hydrogen, linear $C_1$-$C_6$ alkyl, branched $C_3$-$C_6$ alkyl, unsubstituted phenyl or substituted phenyl, and wherein preferably each R independently is hydrogen, methyl or ethyl, and wherein more preferably $NR_4^+$ is tetramethylammonium ion, tetraethylammonium ion or $NH_4^+$, and wherein most preferably $NR_4^+$ is $NH_4^+$. It is particularly preferred that all salts as set forth in items (5), (7) and (8) are salts of $NR_4^+$ as specified.

Therefore, the provision of ammonium salt for one and/or more of the agents as set forth in items (5), (7) and (8) can provide significant further benefits in terms of stabilization and preservation of a blood sample and of facilitating the reliable determination of blood components.

It is particularly advantageous when ammonium salt for one and/or more of the agents as set forth in items (5), (7) and (8) and additionally the ammonium salt iv) as a further additive are provided together in the composition. This way, for example, changes in osmolarity and the outflow of water from the blood cells which would lead to a possible dilution effect and possible impairment of cellular integrity due to the desiccation of blood cells can be even more minimized or avoided. This can lead to an enhanced inhibition of hemolysis and even further improved stabilization of the blood sample.

The composition according to the present invention can comprise a buffer and/or an additive commonly used in the preanalytics of blood and for preserving blood, preferably in a content of up to 50% by weight. Preferably the composition is stable at room temperature and retains its effects for several weeks, more preferably for several months, and most preferably for several years, thus extending shelf life.

In a specific embodiment one and/or more of glucose, lactate and homocysteine are stabilized at room temperature for up to 50 hours after blood collection. However, a temperature from 0° C. to 37° C. and a post-collection time of up to 96 hours are comprised in the method according to the present invention. Unexpectedly and advantageously the method of the present invention stabilizes glucose, lactate and homocysteine simultaneously. In an embodiment wherein the amount of one and/or more of glucose, lactate and homocysteine in blood and/or other blood component(s) are determined the following steps are comprised.

A blood collection device comprising, placed in the device, a composition according to the present invention is provided, followed by placing blood in said blood collection device. Alternatively, blood is placed in a blood collection device and subsequently a composition of the present invention is placed in the blood collection device. The composition of the present invention is mixed with blood in the blood collection device. Optionally the blood is stored in the blood collection device for a predetermined period of time, for example until processing such as centrifugation or analysis and for up to 50, 72 or 96 hours at room temperature, during which glucose, lactate and homocysteine levels are substantially constant. In a further step the amount of one and/or more of glucose, lactate and homocysteine and/or other blood component(s) in the blood sample is determined, for example by using conventional physical, chemical, enzymatic and/or immunological methods, including combinations thereof. Without being limited thereto, analytical methods may comprise gas chromatography (GC), mass spectrometry (MS), gas chromatography-mass spectrometry (GC-MS), gas chromatography-mass spectrometry with isotopic dilution (GC-ID-MS), liquid chromatography (LC), liquid chromatography with mass spectrometry (LC-MS), liquid chromatography with tandem mass spectrometry (LC-MS-MS), high-pressure liquid chromatography (HPLC), high-pressure liquid chromatography with fluorescence detection (HPLC-FD), HPLC with electrochemical detection (HPLC-ED), fluorescence polarization immunoassay (FPIA), chemiluminescence immunoassay (e.g. ICL), enzyme linked immunoassay (EIA), ion-exchange chromatography (IEC), capillary electrophoresis and capillary electrophoresis with laser-induced fluorescence, wherein HPLC and immunoassays are particularly widely used in clinical laboratories.

After the mixing of the composition of the present invention and the blood, the mass concentration of the at least one inhibitor of hexokinase preferably is at least 0.01 mg/mL blood, more preferably is at least 0.02 mg/mL blood, even more preferably is in a range from 0.02 to 25 mg/mL blood and most preferably is in a range from 0.02 to 4 mg/mL blood, the mass concentration of the at least one glycolysis-inhibiting agent preferably is at least 0.01 mg/mL blood, more preferably is at least 0.02 mg/mL blood, even more preferably is in a range from 0.02 to 25 mg/mL blood and most preferably is in a range from 0.02 to 4 mg/mL blood, optionally the mass concentration of the optional anticoagulant preferably is at least 0.01 mg/mL blood, more preferably is at least 0.1 mg/mL blood, even more preferably is in a range from 0.1 to 25 mg/mL blood and most preferably is in a range from 1 to 2.5 mg/mL blood or 12 to 30 IU/mL blood, and preferably the ratio of the mass concentrations of the at least one inhibitor of hexokinase and the at least one glycolysis-inhibiting agent is in a range from 100:1 to 1:100, more preferably is in a range from 50:1 to 1:50, even more preferably is in a range from 25:1 to 1:25 and most preferably is in a range from 10:1 to 1:10. Preferably, whole blood is mixed, and preferably plasma glucose, plasma lactate and plasma homocysteine respectively are determined. Using whole blood and plasma analysis instead of serum is advantageous in that there is no time required to wait for coagulation, there is more sample material and there are no artifacts stemming from coagulation effects such as slight hemolysis or ongoing coagulation after centrifugation. Substantially constant levels preferably are levels which have a time-dependent variation of not more than 4% for glucose and homocysteine and not more than 8% for lactate, more preferably are levels which have a time-dependent variation of not more than 3% for glucose and homocysteine and not more than 5% for lactate, even more preferably are levels which have a time-dependent variation of not more than 2% for glucose and homocysteine and not more than 4% for lactate, yet even more preferably are levels which have a time-dependent variation of not more than 1.5% for glucose and homocysteine and not more than 3% for lactate and most preferably are levels which have a time-dependent variation of not more than 1% for glucose and homocysteine and not more than 2% for lactate.

The composition according to the present invention is preferably provided in solid form, lyophilized form or in solution, and wherein in a case of a solution water or dilute acidic aqueous solution is preferred. In an embodiment dilute acidic aqueous solution is used to enhance the solubility of substances in the composition of the invention, i.e. it is a solvent or a solubilizer. However, in a case of a solution, water is more preferred, because excessive acidification can interfere in the determination of lactate. In an embodiment, the composition of the invention does not contain acid as an additive, more preferably does not contain acid.

In the method for the inhibition of glycolysis and optionally coagulation in a blood sample in vitro blood is mixed after its withdrawal with the composition according to the invention.

Another aspect of the present invention relates to an in vitro diagnostic method, wherein the amount(s) of blood component(s) is (are) determined in a stabilized blood sample mixed with the composition according to the present invention. In particular, one and/or more of glucose, lactate and homocysteine are stabilized, preferably at room temperature for up to 50 hours after blood collection. Preferably glucose, lactate and homocysteine are stabilized simultaneously. The determination of the amount(s) of the respective blood component(s) is carried out using conventional physical, chemical, enzymatic and/or immunological methods, including combinations thereof.

A further aspect of the present invention is the use of the composition of the invention for the inhibition of the glycolytic enzyme system and glycolysis and optionally coagulation in a blood sample in vitro. Unexpectedly, it was found in the present invention that the use of the composition of the present invention efficiently stabilizes any one of glucose, lactate and homocysteine, and any combination thereof, in blood. Even more surprisingly, it was found in the present invention that the use of the composition of the present invention efficiently and advantageously stabilizes glucose, lactate and homocysteine in blood after collection simultaneously. This allows blood glucose, lactate and homocysteine to be determined accurately and reliably using a single sample. According to this aspect of the invention, glucose, lactate and/or homocysteine can be preferably and advantageously stored and transported at room temperature for up to 50 hours, more preferably for up to 72 hours, most preferably for 96 hours after blood collection.

By using antiglycolytic agents according to the present invention and in addition anticoagulant, a blood sample can be stored and transported in a substantially physiologically native state. Room temperature denotes a temperature range from 20° C. to 25° C. However, a temperature above or below room temperature can also be acceptable, and a temperature range from 0° C. to 37° C. lies within the use of the present invention. Moreover and preferably, concurrently with or subsequently to the use of the composition according to the present invention (a) test(s) is (are) carried out for the determination of one and/or more of glucose, lactate and homocysteine and optionally a further blood component. Advantageously a single sample can be used for a multi-analyte analysis, and possible interference from components of the composition of the invention in the analytical testing for glucose, lactate and homocysteine and other co-analytes is preferably substantially avoided and more preferably avoided by choosing components that are compliant or respectively non-interfering in the subsequent tests. The composition according to the present invention can be advantageously used to increase the reliability of diagnosis and prediction. In view of the potential risk of hemolysis and the possible interference with the analyses therefrom, according to a preferred embodiment the ammonium salt iv) is furthermore added to the composition.

Another aspect of the present invention is a blood collection device comprising the composition of the present invention, wherein the blood collection device preferably comprises a device which is capable of being connected with a conventional blood withdrawal device. Conventional blood collection tubes including evacuated blood collection tubes such as vacutainer and aspiration systems such as monovette are known in the art.

In another aspect the invention relates to a use of the blood collection device according to the present invention for stabilizing and/or storing of a blood sample in vitro, wherein preferably the blood sample is stabilized and/or stored at room temperature for up to 50 hours after blood collection. However, a temperature range from 0° C. to 37° C. and a storage time of up to 96 hours are comprised in the invention. This aspect of the present invention provides a particularly efficient use, wherein concurrently or subsequently (a) test(s) is (are) preferably carried out for the determination of one and/or more of glucose, lactate and homocysteine and optionally a further blood component.

A blood collection device comprising, placed in the device, a composition according to the present invention is provided, followed by placing blood in said blood collection device. Alternatively, blood is placed in a blood collection device and subsequently a composition of the present invention is placed in the blood collection device. The composition of the present invention is mixed with blood in the blood collection device. Optionally the blood is stored in the blood collection device for a predetermined period of time, for example until processing such as centrifugation or analysis and for up to 50, 72 or 96 hours at room temperature, during which glucose, lactate and homocysteine levels are substantially constant. In a further step the amount of one and/or more of glucose, lactate and homocysteine and/or other blood component(s) in the blood sample is determined, for example by using conventional physical, chemical, enzymatic and/or immunological methods, including combinations thereof. Without being limited thereto, analytical methods may comprise gas chromatography (GC), mass spectrometry (MS), gas chromatography-mass spectrometry (GC-MS), gas chromatography-mass spectrometry with isotopic dilution (GC-ID-MS), liquid chromatography (LC), liquid chromatography with mass spectrometry (LC-MS), liquid chromatography with tandem mass spectrometry (LC-MS-MS), high-pressure liquid chromatography (HPLC), high-pressure liquid chromatography with fluorescence detection (HPLC-FD), HPLC with electrochemical detection (HPLC-ED), fluorescence polarization immunoassay (FPIA), chemiluminescence immunoassay (e.g. ICL), enzyme linked immunoassay (EIA), ion-exchange chromatography (IEC), capillary electrophoresis and capillary electrophoresis with laser-induced fluorescence, wherein HPLC and immunoassays are particularly widely used in clinical laboratories.

After the mixing of the composition of the present invention and the blood, the mass concentration of the at least one inhibitor of hexokinase preferably is at least 0.01 mg/mL blood, more preferably is at least 0.02 mg/mL blood, even more preferably is in a range from 0.02 to 25 mg/mL blood and most preferably is in a range from 0.02 to 4 mg/mL blood, the mass concentration of the at least one glycolysis-inhibiting agent preferably is at least 0.01 mg/mL blood, more preferably is at least 0.02 mg/mL blood, even more preferably is in a range from 0.02 to 25 mg/mL blood and most preferably is in a range from 0.02 to 4 mg/mL blood, optionally the mass concentration of the optional anticoagulant preferably is at least 0.01 mg/mL blood, more preferably is at least 0.1 mg/mL blood, even more preferably is in a range from 0.1 to 25 mg/mL blood and most preferably is in a range from 1 to 2.5 mg/mL blood or 12 to 30 IU/mL blood, and preferably the ratio of the mass concentrations of the at least one inhibitor of hexokinase and the at least one glycolysis-inhibiting agent is in a range from 100:1 to 1:100, more preferably is in a range from 50:1 to 1:50, even more preferably is in a range from 25:1 to 1:25 and most preferably is in a range from 10:1 to 1:10. Preferably, whole blood is mixed, and preferably plasma glucose, plasma lactate and plasma homocysteine respectively are determined. Using whole blood and plasma analysis instead of serum is advantageous in that there is no time required to wait for coagulation, there is more sample material and there are no artifacts stemming from coagulation effects such as slight hemolysis or ongoing coagulation after centrifugation. Substantially constant levels preferably are levels which have a time-dependent variation of not more than 4% for glucose and homocysteine and not more than 8% for lactate, more preferably are levels which have a time-dependent variation of not more than 3% for glucose and homocysteine and not more than 5% for lactate, even more preferably are levels which have a time-dependent variation of not more than 2% for glucose and homocysteine and not more than 4% for lactate, yet even more preferably are levels which have a time-dependent variation of not more than 1.5% for glucose and homocysteine and not more than 3% for lactate and most preferably are levels which have a time-dependent variation of not more than 1% for glucose and homocysteine and not more than 2% for lactate.

Another aspect of the present invention relates to a kit which comprises the blood collection device of the present invention and test substances for the determination of at least one of, optionally all simultaneously, glucose, lactate and homocysteine and optionally a further blood component in collected blood.

A further aspect of the invention is a composition as set forth in any one of items (1) to (14) for the stabilization of one and/or more of glucose, lactate and homocysteine in blood.

In an embodiment the at least one glycolysis-inhibiting agent ii) is $NH_4F$. The provision of $NH_4F$ is particularly efficient because fluoride ion can contribute to the inhibition of glycolysis, while advantageously at the same time ammonium ion can contribute to inhibiting hemolysis. In particular, fluoride salt is preferably ammonium fluoride because ammonium fluoride can minimize changes in osmolarity and can avoid the outflow of water from the blood cells. Thus a possible dilution effect and possible impairment of cellular integrity due to the desiccation of blood cells can be inhibited.

In another aspect the present invention discloses a use of at least one glycolysis-inhibiting agent for the stabilization and ex vivo determination of homocysteine in blood after withdrawal, wherein the at least one glycolysis-inhibiting agent preferably has activity for an enzyme involved in glucose catabolism, more preferably has antiglycolytic activity for any one of the enzymes in the glycolytic pathway, and most preferably is at least one inhibitor of hexokinase.

Surprisingly, it was found in the present invention that the use of at least one glycolysis-inhibiting agent, and in particular the combinations of agents according to the present invention, not only stabilizes glucose and lactate, but also homocysteine which is a component in sulfur amino acid metabolism. Unexpectedly, the sufficient and improved inhibition of glycolysis inhibits the metabolic processes that lead to the ex vivo formation of homocysteine, presumably involving a change in or an inhibition of intracellular ATP-dependent metabolic processes such as transmethylation reactions of homocysteine precursors.

In the present invention it is considered that particular agents can have a multitude of functions and effects. For example, an antiglycolytic agent can inhibit and/or stimulate several enzymes involved in glucose catabolism at the same time, or also inhibit hemolysis. Such bi- or multi-functionalities are understood to be comprised in the present invention. However, in typical and usually applied embodiments of the present invention, each of these agents is specific and monofunctional for the respective enzyme, i.e. at least one compound for component i), at least another compound for component ii), and optionally again another compound for the optional component iii) of the composition as set forth in claim 1 are present, while furthermore optionally ammonium salt $NR_4X$ iv) as set forth in claim 3 is present.

The following examples are merely illustrative of the present invention and they should not be considered as limiting the scope of the invention in any way. The examples and modifications or other equivalents thereof will become apparent to those skilled in the art in the light of the present entire disclosure.

BRIEF DESCRIPTION OF THE FIGURES

FIG. 2 depicts lactate stability at room temperature in whole blood containing A: 2-deoxy-D-glucose, ammonium fluoride and ammonium heparinate; B: 2-deoxy-D-glucose, ammonium fluoride and sodium heparinate; C: 2-deoxy-D-glucose, ammonium fluoride and potassium salt of EDTA; and D: potassium salt of EDTA.

FIG. 3 shows homocysteine stability at room temperature in whole blood containing A: 2-deoxy-D-glucose, ammonium fluoride and ammonium heparinate; B: 2-deoxy-D-glucose, ammonium fluoride and sodium heparinate; C: 2-deoxy-D-glucose, ammonium fluoride and potassium salt of EDTA; and D: potassium salt of EDTA.

EXAMPLES AND COMPARATIVE EXAMPLES

Figure 1:
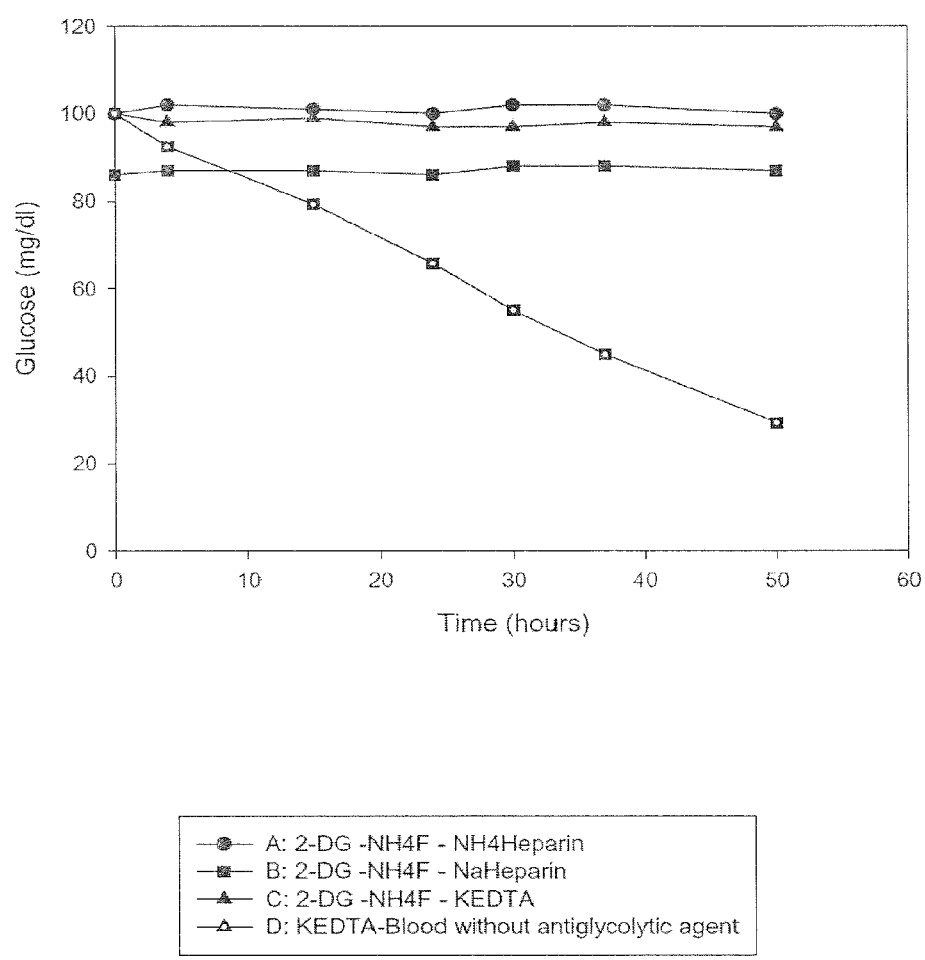
FIG. 1 shows glucose stability at room temperature in whole blood containing A: 2-deoxy-D-glucose, ammonium fluoride and ammonium heparinate; B: 2-deoxy-D-glucose, ammonium fluoride and sodium heparinate; C: 2-deoxy-D-glucose, ammonium fluoride and potassium salt of EDTA; and D: potassium salt of EDTA.

Materials Used and Method
Materials

Iodoacetate, ammonium fluoride, dichloroacetic acid, 3-bromopyruvic acid, 2-deoxy-D-glucose, and sodium oxamate were purchased from SIGMA (SIGMA-ALDICH, Germany). Blood collection tubes with anticoagulants were provided by KABE (KABE Labortechnik GmbH, Germany)

Blood Collection and Sampling Protocol

Before blood collection, particular mixtures of antiglycolytic agents were added into blood collection tubes containing anticoagulant. The respective concentrations of the antiglycolytic agents in the mixtures were in a range from 0.02 mg to 4 mg/mL of blood to be mixed with. Anticoagulant used was ammonium, lithium or sodium heparinate at a concentration of 12.5 IU/mL or dipotassium ethylene diamine tetraacetic acid (K2EDTA) at a concentration of 2 mg/mL.

Blood was drawn from healthy volunteers by venipuncture of the antecubital vein by aspiration. Blood samples were collected into tubes with or without the particular mixtures of antiglycolytic agents. Caution was taken that all tubes were filled to the mark and that the blood was well mixed with the agents by inverting the tubes 4 times immediately after blood collection.

After whole blood was mixed with different antiglycolytic agents and/or anticoagulants in the tubes, the tubes were stored at room temperature (from 20 to 25° C.) for different time intervals before centrifugation. The tubes were centrifuged 4, 15, 24, 48 and 50 hours after blood collection, and the separated plasma was stored at −20° C. until analysis. Concentrations of glucose, lactate and homocysteine were determined for the samples centrifuged after the different time intervals of storage.

As a control and for comparison, a blood sample without any antiglycolytic agent was centrifuged immediately after blood collection and the plasma was separated within 10 min and stored at −20° C. until analysis. Glucose, lactate and homocysteine concentrations were determined for this sample, said concentrations being defined as the reference concentrations at time 0. Percentages for the time-dependent glucose, lactate and homocysteine concentrations relative to the reference concentrations (baseline) were computed.

Measurement of Glucose

The hexokinase method on cobas c (Roche Diagnostics) was used according to the protocol of the manufacturer.

Measurement of Lactate

A colorimetric method on cobas c (Roche Diagnostics) was used. The method is based on the oxidation of lactate to pyruvate by lactate oxidase.

Measurement of Total Homocysteine (tHcy)

tHcy was measured by a competitive immunoassay on IMMULITE (SIEMENS, Germany) and by the Diazyme Homocysteine Enzymatic Assay Kit on cobas c (Roche Diagnostics).

Example 1

Whole blood was added to 2-deoxy-D-glucose (2.9 mg/mL blood), ammonium fluoride (2.9 mg/mL blood) and an anticoagulant in different aqueous solutions (solvents were Solvent 1: $H_2O$; and Solvent 2: aq. ac.=weakly acidified aqueous solution, respectively). After different time intervals glucose, lactate and homocysteine concentrations were determined. The determined values are shown in Table 1 as percentages of the baseline. The combination of 2-deoxy-D-glucose and ammonium fluoride stabilized glucose, lactate and homocysteine fast, efficiently and continuously.

TABLE 1

| analyte | solvent | changes in plasma analyte concentration time intervals (hours) | | | | |
|---|---|---|---|---|---|---|
| | | 0 | 4 | 15 | 24 | 48 |
| glucose | H$_2$O | 100 | 101 | 101 | 100 | 101 |
| glucose | aq. ac. | 100 | 102 | 100 | 102 | 102 |
| lactate | H$_2$O | 100 | 107 | 107 | 108 | 107 |
| lactate | aq. ac. | 100 | 102 | 104 | 104 | 104 |
| homocysteine | H$_2$O | 100 | 100 | 100 | 102 | 100 |
| homocysteine | aq. ac. | 100 | 101 | 101 | 100 | 100 |

For whole blood with 2-deoxy-D-glucose and ammonium fluoride, ammonium heparinate (A), sodium heparinate (B) and potassium salt of EDTA (C) were used respectively as anticoagulant. For the anticoagulants A-C it was found that glucose, lactate and homocysteine were stabilized fast, efficiently and continuously, as can be seen in FIGS. 1-3.

Example 2

Whole blood was added to 2-deoxy-D-glucose (2.9 mg/mL blood), sodium iodoacetate (1.13 mg/mL blood) and an anticoagulant in different aqueous solutions (solvents were Solvent 1: H$_2$O; and Solvent 2: aq. ac.=weakly acidified aqueous solution, respectively). After different time intervals glucose, lactate and homocysteine concentrations were determined. The determined values are shown in Table 2 as percentages of the baseline. The combination of 2-deoxy-D-glucose and sodium iodoacetate stabilized glucose, lactate and homocysteine fast, efficiently and continuously.

TABLE 2

| analyte | solvent | changes in plasma analyte concentration time intervals (hours) | | | | |
|---|---|---|---|---|---|---|
| | | 0 | 4 | 15 | 24 | 48 |
| glucose | H$_2$O | 100 | 100 | 100 | 101 | 100 |
| glucose | aq. ac. | 100 | 101 | 102 | 101 | 101 |
| lactate | H$_2$O | 100 | 97 | 97 | 98 | 97 |
| lactate | aq. ac. | 100 | 101 | 102 | 101 | 101 |
| homocysteine | H$_2$O | 100 | 100 | 100 | 101 | 100 |
| homocysteine | aq. ac. | 100 | 103 | 103 | 101 | 103 |

Example 3

Whole blood was added to 2-deoxy-D-glucose (2.9 mg/mL blood), sodium oxamate (1.25 mg/mL blood) and an anticoagulant in weakly acidified aqueous solution as solvent. After different time intervals glucose and homocysteine concentrations were determined. The determined values are shown in Table 3 as percentages of the baseline. The combination of 2-deoxy-D-glucose and sodium oxamate stabilized glucose and homocysteine fast, efficiently and continuously.

TABLE 3

| analyte | changes in plasma analyte concentration time intervals (hours) | | | | |
|---|---|---|---|---|---|
| | 0 | 4 | 15 | 24 | 48 |
| glucose | 100 | 100 | 100 | 100 | 100 |
| homocysteine | 100 | 102 | 108 | 112 | 112 |

Example 4

Whole blood was added to 3-bromopyruvic acid (2.5 mg/mL blood), sodium iodoacetate (1.13 mg/mL blood) and an anticoagulant in water and weakly acidified aqueous solution as solvent respectively. After different time intervals glucose concentrations were determined. The determined values are shown in Table 4 as percentages of the baseline. The combination of 3-bromopyruvic acid and sodium iodoacetate stabilized glucose fast, efficiently and continuously.

TABLE 4

| solvent | changes in plasma glucose concentration time intervals (hours) | | | | |
|---|---|---|---|---|---|
| | 0 | 4 | 15 | 24 | 48 |
| H$_2$O | 100 | 100 | 101 | 100 | 100 |
| aq. ac. | 100 | 104 | 104 | 104 | 104 |

Example 5

Whole blood was added to 2-deoxy-D-glucose (2.9 mg/mL blood), ammonium fluoride (2.9 mg/mL blood), sodium oxamate (0.81 mg/mL blood) and an anticoagulant in weakly acidified aqueous solution as solvent. After different time intervals glucose, lactate and homocysteine concentrations were determined. The determined values are shown in Table 5 as percentages of the baseline. The combination of 2-deoxy-D-glucose, ammonium fluoride and sodium oxamate stabilized glucose, lactate and homocysteine fast, efficiently and continuously.

TABLE 5

| analyte | changes in plasma analyte concentration time intervals (hours) | | | | |
|---|---|---|---|---|---|
| | 0 | 4 | 15 | 24 | 48 |
| glucose | 100 | 102 | 102 | 103 | 102 |
| lactate | 100 | 96 | 96 | 96 | 97 |
| homocysteine | 100 | 104 | 103 | 104 | 103 |

Example 6

Whole blood was added to 2-deoxy-D-glucose (2.9 mg/mL blood), sodium iodoacetate (1.2 mg/mL blood), sodium oxamate (0.65 mg/mL blood) and an anticoagulant in weakly acidified aqueous solution as solvent. After different time intervals glucose and lactate concentrations were determined. The determined values are shown in Table 6 as percentages of the baseline. The combination of 2-deoxy-D-glucose, sodium iodoacetate and sodium oxamate stabilized glucose and lactate fast, efficiently and continuously.

TABLE 6

| analyte | changes in plasma analyte concentration time intervals (hours) | | | | |
|---|---|---|---|---|---|
| | 0 | 4 | 15 | 24 | 48 |
| glucose | 100 | 102 | 101 | 102 | 102 |
| lactate | 100 | 98 | 97 | 98 | 98 |

Comparative Example 1

When whole blood was mixed with potassium salt of EDTA only, i.e. no antiglycolytic agent was added, glucose, lactate and homocysteine were not stabilized. The glucose concentration decreased rapidly and continuously (see FIG. 1), while the lactate and homocysteine concentrations increased rapidly and continuously (see FIGS. 2-3).

Comparative Example 2

Whole blood was added to Sarstedt blood collection tubes containing sodium fluoride and potassium oxalate. After different time intervals glucose and lactate concentrations were determined. The determined values are shown in Table 7 as percentages of the baseline. Glucose and lactate concentrations were not sufficiently stabilized, in any event remarkably less than in the Examples according to the present invention. The glucose concentration decreased significantly and continuously, while the lactate concentration increased significantly and continuously.

TABLE 7

| | changes in plasma analyte concentration time intervals (hours) | | | | |
|---|---|---|---|---|---|
| analyte | 0 | 4 | 15 | 24 | 48 |
| glucose | 100 | 96 | 94 | 92 | 91 |
| lactate | 100 | 106 | 110 | 113 | 116 |

Comparative Example 3

Whole blood was added to 2-deoxy-D-glucose (2.9 mg/mL blood) and an anticoagulant in weakly acidified aqueous solution as solvent. After different time intervals glucose and homocysteine concentrations were determined. The determined values are shown in Table 8 as percentages of the baseline. Glucose and homocysteine concentrations were not sufficiently stabilized. The glucose concentration decreased significantly and continuously, while the homocysteine concentration increased significantly and continuously.

TABLE 8

| | changes in plasma analyte concentration time intervals (hours) | | | | |
|---|---|---|---|---|---|
| analyte | 0 | 4 | 15 | 24 | 48 |
| glucose | 100 | 87 | 85 | 80 | 80 |
| homocysteine | 100 | 102 | 106 | 117 | 117 |

Comparative Example 4

Whole blood was added to 3-bromopyruvic acid (2.5 mg/mL blood) and an anticoagulant in weakly acidified aqueous solution as solvent. After different time intervals glucose and homocysteine concentrations were determined. The determined values are shown in Table 9 as percentages of the baseline. Glucose and homocysteine concentrations were not sufficiently stabilized. The glucose concentration decreased significantly and continuously, while the homocysteine concentration increased significantly and continuously.

TABLE 9

| | changes in plasma analyte concentration time intervals (hours) | | | | |
|---|---|---|---|---|---|
| analyte | 0 | 4 | 15 | 24 | 48 |
| glucose | 100 | 90 | 89 | 88.8 | 88 |
| homocysteine | 100 | 101 | 111 | 111 | 111 |

A comparison of the Examples with the Comparative Examples shows that the compositions according to the present invention stabilize glucose, lactate and homocysteine fast, efficiently and continuously, whereas compositions not containing the particular combinations of agents according to the present invention are insufficient in stabilizing glucose, lactate and homocysteine—even when agents are used that inhibit hexokinase such as 2-deoxy-D-glucose (see Comparative Example 3) and 3-bromopyruvic acid (see Comparative Example 4) alone.

Examples 7-13 and Comparative Example 5

In vitro hemolysis was tested in blood samples incubated at room temperature (22° C.-25° C.) by determining the free plasma hemoglobin concentration (g/L) over time (0-50 hours), wherein blood samples were mixed with different compositions.

Example 7

Whole blood was added to 2-deoxy-D-glucose, sodium iodoacetate, sodium oxamate and $K_3$EDTA.

Example 8

Whole blood was added to 2-deoxy-D-glucose, ammonium salt of iodoacetic acid, sodium oxamate and $K_3$EDTA.

Example 9

Whole blood was added to 2-deoxy-D-glucose, sodium iodoacetate, ammonium salt of oxamic acid and $K_3$EDTA.

Example 10

Whole blood was added to 2-deoxy-D-glucose, sodium iodoacetate, sodium oxamate, $K_3$EDTA and tetraethylammonium chloride.

Example 11

Whole blood was added to 2-deoxy-D-glucose, sodium iodoacetate, sodium oxamate, $K_3$EDTA and tetramethylammonium fluoride.

Example 12

Whole blood was added to 2-deoxy-D-glucose, sodium iodoacetate, sodium oxamate, $K_3$EDTA and tetramethylammonium chloride.

Example 13

Whole blood was added to 2-deoxy-D-glucose, sodium iodoacetate, sodium oxamate, $K_3$EDTA and ammonium chloride.

Comparative Example 5

Whole Blood was added to K$_3$EDTA

The concentrations of antiglycolytic agents in the mixtures were 0.1-4 mg/mL blood. In the cases of Examples 10-13, 0.5-1 µmol of the respective ammonium salts per mL blood were added to the mixture.

TABLE 10

| | Free plasma hemoglobin concentration (g/L) time intervals (hours) | | | |
|---|---|---|---|---|
| | 0 | 1.5 | 3.5 | 50 |
| Comparative Example 5 | 0.290 | 0.290 | 0.300 | 0.370 |
| Example 7 | 0.270 | 0.275 | 0.290 | 0.330 |
| Example 8 | 0.200 | 0.210 | 0.210 | 0.210 |
| Example 9 | 0.245 | 0.250 | 0.250 | 0.250 |
| Example 10 | 0.150 | 0.150 | 0.154 | 0.160 |
| Example 11 | 0.220 | 0.220 | 0.230 | 0.232 |
| Example 12 | 0.280 | 0.280 | 0.280 | 0.280 |
| Example 13 | 0.290 | 0.290 | 0.290 | 0.290 |

Comparative Example 5 shows that when whole blood is mixed with only K$_3$EDTA, over time a significant degree of hemolysis occurs, as seen in the increase of the free plasma hemoglobin concentration at 3.5 hours and especially at 50 hours.

In Example 7, which does not contain any ammonium salt, hemolysis is also observed, but to a lesser extent at 50 hours compared to Comparative Example 5.

Examples 8-9 demonstrate that when the combination of antiglycolytic agents comprises salts, hemolysis can unexpectedly and advantageously be significantly inhibited by providing at least one salt of said agents as an ammonium salt.

Surprisingly, hemolysis can also be efficiently and effectively inhibited by adding to the composition as a further component an ammonium salt, as shown in Examples 10-13.

Therefore, the provision of an ammonium salt, as one or more of the antiglycolytic agents according to the invention and/or as a further additive, provides significant further benefits. One and/or more of glucose, lactate and homocysteine, preferably all, in the blood sample is (are) stabilized, while furthermore the inhibition of hemolysis can be significantly enhanced. This particularly advantageous stabilization and preservation of the blood samples in turn can facilitate an improved determination of blood components and reliable diagnostics.

The invention claimed is:

1. A blood collection device comprising a composition comprising in combination and commonly placed in the blood collection device:

i) at least one inhibitor of hexokinase, selected from the group consisting of 2-deoxy-D-glucose, 2-fluoro-2-deoxy-D-glucose, 2-amino-2-deoxy-D-glucose and 3-bromopyruvic acid or salt thereof;

ii) at least one glycolysis-inhibiting agent having activity for another enzyme involved in glucose catabolism, selected from the group consisting of fluoride salt, iodoacetic acid or salt therof, oxamic acid or salt thereof and dichloroacetic acid or salt therof; and optionally iii) an anticoagulant and/or a plasma stabilizer, selected from the group consisting of EDTA salt, citrate salt, oxalate salt and heparin salt.

2. The blood collection device according to claim 1, wherein the composition further comprises iv) ammonium salt NR$_4$X, wherein each R independently is hydrogen, linear C$_1$-C$_6$ alkyl, branched C$_3$-C$_6$ alkyl, unsubstituted phenyl or substituted phenyl, and X is halide, hydroxide, C$_1$-C$_4$ alkoxide and acetate.

3. The blood collection device according to claim 1, wherein the at least one glycolysis-inhibiting agent ii) has antiglycolytic activity for any one of the enzymes in the glycolytic pathway downstream of hexokinase.

4. The blood collection device according to claim 1, further comprising a blood sample which is preserved for further analysis.

5. The blood collection device according to claim 4, wherein one and/or more of glucose, lactate and homocysteine in the blood sample is stabilized.

6. The blood collection device according to claim 4, wherein the mass concentration of the at least one inhibitor of hexokinase i) is at least 0.01 mg/mL blood sample and wherein the mass concentration of the at least one glycolysis-inhibiting agent ii) is at least 0.01 mg/mL blood sample.

7. The blood collection device according to claim 1, wherein the composition is substantially free of agents for the lysis of blood cells.

8. The blood collection device according to claim 1, comprising a device which is capable of being connected with a conventional blood withdrawal device.

9. The blood collection device according to claim 1, which is a blood collection tube, an evacuated blood collection tube, a vacutainer or an aspiration system respectively enclosing said composition.

10. The blood collection device according to claim 1, combined within a kit further comprising test substances for the determination of at least one of, optionally all simultaneously, glucose, lactate and homocysteine and optionally a further blood component in collected blood.

* * * * *